United States Patent
Nguyen et al.

(10) Patent No.: US 12,059,580 B2
(45) Date of Patent: Aug. 13, 2024

(54) METHOD AND SYSTEM FOR GUIDED RADIATION THERAPY

(71) Applicants: Doan Trang Nguyen, Meadowbank (AU); Paul Keall, Greenwich (AU); Adam Mylonas, Baulkham Hills (AU)

(72) Inventors: Doan Trang Nguyen, Meadowbank (AU); Paul Keall, Greenwich (AU); Adam Mylonas, Baulkham Hills (AU)

(73) Assignee: SEETREAT PTY LTD, Greenwich (AU)

( * ) Notice: Subject to any disclaimer, the term of this patent is extended or adjusted under 35 U.S.C. 154(b) by 931 days.

(21) Appl. No.: 16/978,847

(22) PCT Filed: Mar. 8, 2019

(86) PCT No.: PCT/AU2019/050212
§ 371 (c)(1),
(2) Date: Sep. 8, 2020

(87) PCT Pub. No.: WO2019/169455
PCT Pub. Date: Sep. 12, 2019

(65) Prior Publication Data
US 2021/0038921 A1    Feb. 11, 2021

(30) Foreign Application Priority Data

Mar. 8, 2018  (AU) ............................... 2018900755

(51) Int. Cl.
*A61N 5/10*    (2006.01)
*A61B 6/00*    (2024.01)
(Continued)

(52) U.S. Cl.
CPC ............ *A61N 5/1067* (2013.01); *A61B 90/39* (2016.02); *A61N 5/1049* (2013.01); *G06N 3/08* (2013.01); *G06T 7/70* (2017.01); *G16H 20/40* (2018.01); *G16H 30/20* (2018.01); *G16H 30/40* (2018.01); *A61B 2090/3966* (2016.02); *A61N 2005/1061* (2013.01); *G06T 2207/20021* (2013.01);
(Continued)

(58) Field of Classification Search
CPC ................ A61N 5/1067; A61N 5/1049; A61N 2005/1061; A61B 90/39; A61B 2090/3966; G16H 20/40; G16H 30/20; G16H 30/40; G06T 2207/20021; G06T 7/70; G06T 2207/20081; G06T 2207/20084; G06N 3/08
See application file for complete search history.

(56) References Cited

U.S. PATENT DOCUMENTS 9,764,162 B1 * 9/2017 Willcut ................. G06T 7/0014
2007/0041494 A1 * 2/2007 Ruchala ............... A61N 5/1048
378/65

(Continued)

*Primary Examiner* — Thaddeus B Cox
*Assistant Examiner* — Joshua Daryl D Lannu
(74) *Attorney, Agent, or Firm* — WC&F IP

(57) ABSTRACT

The present invention is concerned with a method and system for guiding a radiation therapy system. The method comprises: capturing an image of a target area to which radiation is to be delivered; analysing the image with a trained convolutional neural network to determine the position of one or more objects of interest present in the target area; and outputting the determined position/s to the radiation therapy system.

19 Claims, 9 Drawing Sheets

(51) Int. Cl.
    *A61B 6/03* (2006.01)
    *A61B 90/00* (2016.01)
    *G06N 3/08* (2023.01)
    *G06T 7/70* (2017.01)
    *G16H 20/40* (2018.01)
    *G16H 30/20* (2018.01)
    *G16H 30/40* (2018.01)

(52) U.S. Cl.
    CPC .............. *G06T 2207/20081* (2013.01); *G06T 2207/20084* (2013.01)

(56) References Cited

U.S. PATENT DOCUMENTS

2016/0035108 A1\* 2/2016 Yu .......................... A61B 5/721
                                                       382/131
2016/0174902 A1\* 6/2016 Georgescu ........... G06V 10/454
                                                       600/408

\* cited by examiner

METHOD AND SYSTEM FOR GUIDED RADIATION THERAPY

FIELD OF THE INVENTION

The present disclosure relates to methods and systems for use in relation to guided radiation therapy systems. In one form, there is disclosed a method and system for guiding a radiation therapy system by reference to the position of fiducial markers implanted in the tumour that is to be radiated.

BACKGROUND OF THE INVENTION

Radiation therapy is a treatment modality used to treat localised tumours. It generally involves producing high energy megavoltage (MV) and conformal beams of x-rays to the target (tumour) using a medical linear accelerator. The radiation interacts with the tissues to create double strand DNA breaks to kill tumour cells. Radiation therapy requires high precision to deliver the dose to the tumour and spare healthy tissue, particularly that of organs surrounding the tumour. Each treatment is tailored to the individual patient.

Advances in radiation therapy techniques, such as intensity modulated radiation therapy (IMRT) and image guided radiation therapy (IGRT) have resulted in improved delivery of radiation doses to tumours while reducing normal tissue toxicity. According to current practices, IGRT is routinely applied at the start of treatment to align the target with its planned position. However, tumours in the thorax, abdomen and pelvis are not static during treatment; a phenomenon known as 'intrafraction motion'. Intrafraction motion occurs when patients move while on the treatment bed (both during setup and treatment) or when organs and tumours move in response to breathing. Real-time image guided adaptive radiation therapy (IGART) systems have been developed at least in part to account for this intrafraction motion.

Certain IGRT and IGART systems operate in real-time by utilising kilovoltage (kV) images for the tracking of fiducial markers implanted in tumours. One such system is known as Kilovoltage Intrafraction Monitoring (KIM). KIM is a real-time image guidance technique that utilises existing radiotherapy technologies found in cancer care centres (i.e. on-board x-ray images). KIM exploits fiducial markers implanted inside the tumour (organ) and reconstructs their location by acquiring multiple images of the target using the on-board kilovoltage (KV) beam (which is a low energy X-ray imager) and determining any motion in the left-right (LR), superior-inferior (SI), and anterior-posterior (AP) directions. KIM Tracking has also been developed, which dynamically modifies the position of a multi leaf collimator (MLC) while delivering the treatment dose based on the tumour position reconstructed by KIM. In KIM, tumour motion is monitored in real-time while both the MV beam is delivering the treatment dose, and the KV beam is imaging the tumour target. If significant motion away from the treatment beam occurs, the treatment is paused and the patient is repositioned before the treatment is continued.

Such real-time IGRT systems typically require accurate segmentation methods to detect and track the fiducial markers, with these methods currently being based on the approach of 'template matching'. Template matching involves detecting a marker in an image by the use of a template image that represents the marker (Campbell et. al. 2017. *Automated target tracking in kilovoltage images using dynamic templates of fiducial marker clusters*, Medical Physics 44 364-374) In turn, the template of a marker is typically based upon a priori knowledge of the marker properties (e.g its shape and size). Typically for regular shaped markers (eg spherical and cylindrical gold), templates are built based on known properties of the marker such as dimensions. Other types of markers such as coiled markers (e.g Visicoil™ and IBA Dosimetry) can be used to decrease migration, however, they are subject to deformation into an arbitrary shape upon implantation resulting in unknown marker properties. In these circumstances, an additional learning period is required to determine the marker properties and develop a template.

While methods are being developed to automatically produce templates without such a priori knowledge, (Fledelius, 2011, et al, *Robust automatic segmentation of multiple implanted cylindrical gold fiducial markers in cone-beam CT projections*. Medical Physics 38. 6351-6361; Poulsen et al 2011, Bertholet et at. 2017), these require this additional learning period during which the marker orientation is learned on the fly. Having a learning period runs the risk of the patient receiving unnecessary radiation.

In addition, many CT images have insufficient resolution and include metal artefacts from the markers. As such, templates typically cannot be constructed prior to treatment, but are instead usually generated online before the time of MV beam-on. For arbitrarily shaped markers, four to five projections with reasonable angular separation are typically required to generate the requisite template. As noted above, this learning period has the drawback of subjecting a patient to unnecessary radiation, namely that delivered to the patient for the purpose of imaging.

The present invention aims to provide an alternative approach to segmentation for use in real-time systems.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In a first aspect there is provided a method for guiding a radiation therapy system, comprising:
  capturing an image of a target area to which radiation is to be delivered;
  analysing the image with a trained convolutional neural network to determine the position of one or more objects of interest present in the target area; and
  outputting the determined position/s to the radiation therapy system.

At least in preferred embodiments, the present invention is concerned with a radiation therapy control system that utilises a deep learning convolutional neural network (CNN) to classify objects of interest (such as fiducial markers in kV images) and thereby determine their position. More specifically, the present invention includes the training of a CNN (typically conducted using images of an anthropomorphic phantom and previous images) to initially differentiate between 'marker' and 'background' regions of the image. The thus trained CNN is then utilised in a tracking system to efficiently track the position of the object of interest in a series of images, in close to or in real time.

In preferred embodiments of the invention when used to track fiducial markers, the present invention allows for the tracking of arbitrarily shaped markers present in fluoroscopic images.

In addition to fiducial markers, the present invention can also be used to track objects of interest such as tumours and intrinsic anatomical features.

In contrast to the template-based approaches of the prior art, the present invention requires no a priori knowledge of the marker properties (such as shape, size and orientation) for set up for a new patient. This obviates the requirement for imaging to be completed ahead of time in order to determine the position and orientation of the fiducial marker, thus reducing the overall quantity of radiation to which the patient is exposed during treatment. The present invention, at least in preferred embodiments, also has the advantage over template-based approaches of being a more robust solution to overlapping and arbitrarily-shaped markers.

The present invention is applicable to tumour motion tracking during external beam radiotherapy with a variety of linear accelerators, including those from Varian Medical Systems and Elektra Medical Systems.

The step of analysing may include:
  generating a tracking window respectively circumscribing each object of interest by utilising a previously determined position for each fiducial marker; and
  applying the convolutional neural network to the interior of each tracking window.

Preferably, the previously determined position is determined from an earlier application of the convolutional neural network. Alternatively, the previously determined position can be determined from earlier CT images of the same patient acquired prior to treatment.

Typically, the object of interest is substantially centered in the tracking window.

The position of the object of interest may be determined by:
  classifying regions of the tracking window as including or not including an object of interest; and
  determining the centroid of connected regions classified as including an object of interest.

Preferably, the regions are defined by traversing the tracking window with a window of smaller dimension than the tracking window.

Typically, the regions are normalised and rescaled prior to undergoing classification.

The present invention has application to the analysis of kV images and with use in image-guided radiation therapy systems.

According to some embodiments, the convolutional neural network includes three convolutional layers, two pooling layers, one fully connected layer and optionally a plurality of batch normalisation layers and rectified linear units.

The method may include the further step of identifying the target area to which radiation is to be delivered on the basis of the output object position/s.

Optionally, the method includes the further step of directing a treatment beam from the radiation therapy system based on a position of the identified target area.

The target area may be tracked by reference to successive output of object positions over time and directing the beam at the target based on said tracking. In this regard, directing the beam based on the estimated position may include adjusting or setting one or more of the following parameters of the radiation therapy system:
  at least one geometrical property of said at least one emitted beam;
  a position of the target relative to the beam;
  a time of emission of the beam; and
  an angle of emission of the beam relative to the target area about a system rotational angle.

According to another aspect of the present invention, there is provided a system for guided radiation therapy including:
  a radiation source for emitting at least one treatment beam of radiation;
  an imaging system arranged to generate a succession of images of a target area to which the treatment beam is to be directed; and
  a control system configured to:
    receive images from the imaging system;
    analyse the images with a trained convolutional neural network to determine the position of one or more objects of interest present in the target area;
    adjust the guided radiation therapy system to direct the treatment beam at the target area.

According to another aspect of the present invention, there is provided a computer software product comprising a sequence of instructions storable on one or more computer-readable storage media, said instructions when executed by one or more processors, cause the processor to:
  receive an image from a radiation therapy system of a target area to which radiation is to be delivered;
  analyse the image with a trained convolutional neural network to determine the position of one or more objects of interest present in the target area; and
  output the fiducial marker position/s to the radiation therapy system.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
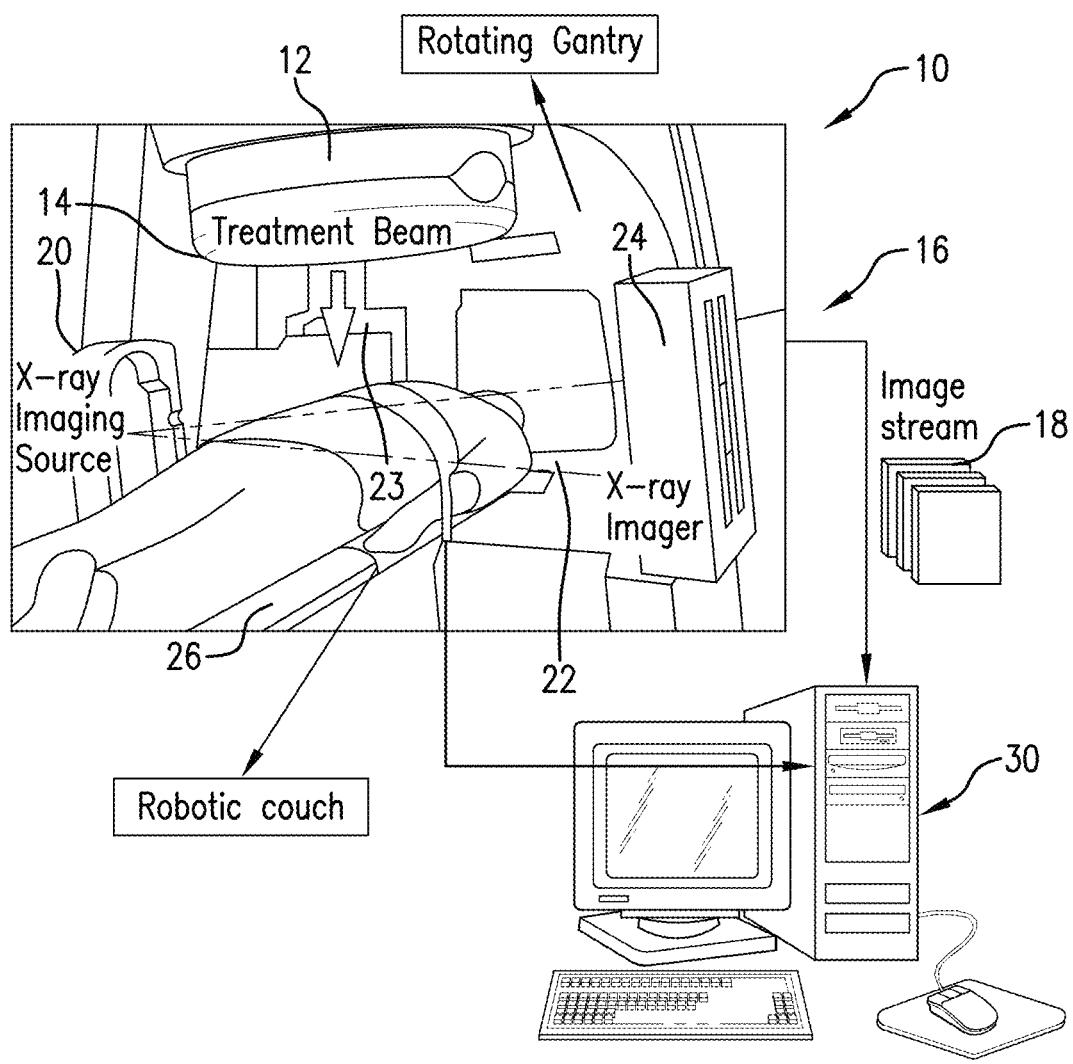
FIG. 1 illustrates a schematic representation of a system configured to implement an embodiment of the present invention.

FIG. 1, depicts a system for image guided radiation therapy able to implement an embodiment of the inventions described herein. The system 10 includes:

- A radiation source 12 for emitting at least one treatment beam of radiation. The radiation source emits the treatment beam 14 along a first beam axis towards the patient being treated. Typically the radiation source 12 will comprise a linear accelerator emitting megavolt x-rays.
- An imaging system 16 arranged to generate a succession of images 18 comprising a two dimensional projection of a field of view and in which the location of the target may be identified. The imaging system 16 includes a second radiation source 20 that emits at least one imaging beam 22 along a second beam axis. The imaging beam 22 will be transmitted in a direction orthogonal to the treatment beam 14. The imaging beam is transmitted through the patient (or at least through the region of the patient) to a radiation detector 24 that is configured to detect radiation transmitted through the target. The spatial intensity of the received radiation is converted to an x-ray image that is a projection of said at least one imaging beam in a plane normal to the direction its emission. Typically, the imaging system will be a kilovolt imaging system built into the linear accelerator. In embodiments of the present invention, the imaging system is arranged to only intermittently emit its imaging beam to thereby reduce the patient's radiation exposure compared to continuous imaging. The rate of imaging can vary depending on requirements or system configuration, but will typically have an imaging interval between 0.1 s to 60s. Some embodiments may have a longer imaging interval.
- A support platform 26 (e.g. a bed) on which the subject of the radiation therapy is supported during treatment. Support platform 26 is repositionable relative to the imaging system and radiation source, so that the patient can be positioned with the centre of the target (i.e. tumour) located as near as possible to the intersection between the first and second beam axes.
- A control system 30 that controls the parameters of operation of the radiation therapy system. Generally speaking, the control system 30 is a computer system comprising one or more processors with associated working memory, data storage and other necessary hardware, that operates under control of software instructions to receive input data from one or more of a user, other components of the system (e.g. the imaging system 16), and outputs control signals to control the operation of the radiation therapy system. Amongst other things, the control system 30 causes the radiation source 12 to direct its at least one treatment beam at the target. To do this, the control system receives images from the imaging system, analyses those images to determine the position of fiducial markers present in the target (thereby estimating the motion of the target), and then issues a control signal to adjust the system 10 to better direct the treatment beam 14 at the target.

As will be appreciated by those skilled in the art, the radiation source 12, imaging system 16 and support platform 30 are common to most conventional image radiation therapy systems. Accordingly, in the conventional manner the radiation source 12 and imaging system 16 can be rotatably mounted (on a structure commonly called a gantry) with respect to the patient support platform 30 so that they can rotate about the patient in use. The rotational axis of the gantry motion is typically orthogonal to the directions of the treatment beam and imaging beam (i.e. the first and second directions.) This enables sequential treatment and imaging of the patient at different angular positions about the system's gantry's axis.

As noted above, the control system 30 processes images received from the imaging system 16 to estimate the motion of the target, and then issues a control signal to adjust the system 10 to better direct the treatment beam at the target. The adjustment typically comprises at least one of the following: changing a geometrical property of the treatment beam such as its shape or position, e.g. by adapting a multi-leaf collimator of the linac; changing the time of emission of the beam, e.g. by delaying treatment beam activation to a more suitable time; gating the operation of the beam, e.g. turning off the beam if the estimated motion is greater than certain parameters; changing an angle at which the beam is emitted relative to the target about the system rotational axes. The system 10 can also be adjusted so as to better direct the treatment beam at the target by moving the patient support platform 26. Moving the support platform 26 effectively changes the position of the centroid of the target with respect to the position of the treatment beam 14 (and imaging beam).

In use, the general method of operation of the system 10 is as follows. The radiation source and imaging system rotates around the patient during treatment. The imaging system acquires 2D projections of the target separated by an appropriate time interval. As discussed above, the target (tumour) will be marked by the placement of fiducial markers within or about the target. The positioning of the markers may be such that the centroid of the markers lies at the centre of the target, but this is not strictly necessary. The control system 30 uses the periodically received 2D projections (e.g. kV X-ray images) to estimate the tumour's position. The control system therefore needs a mechanism for determining the position of the fiducials and then performing ongoing estimation of the target's location and orientation in 3-dimensions.

Figure 2:
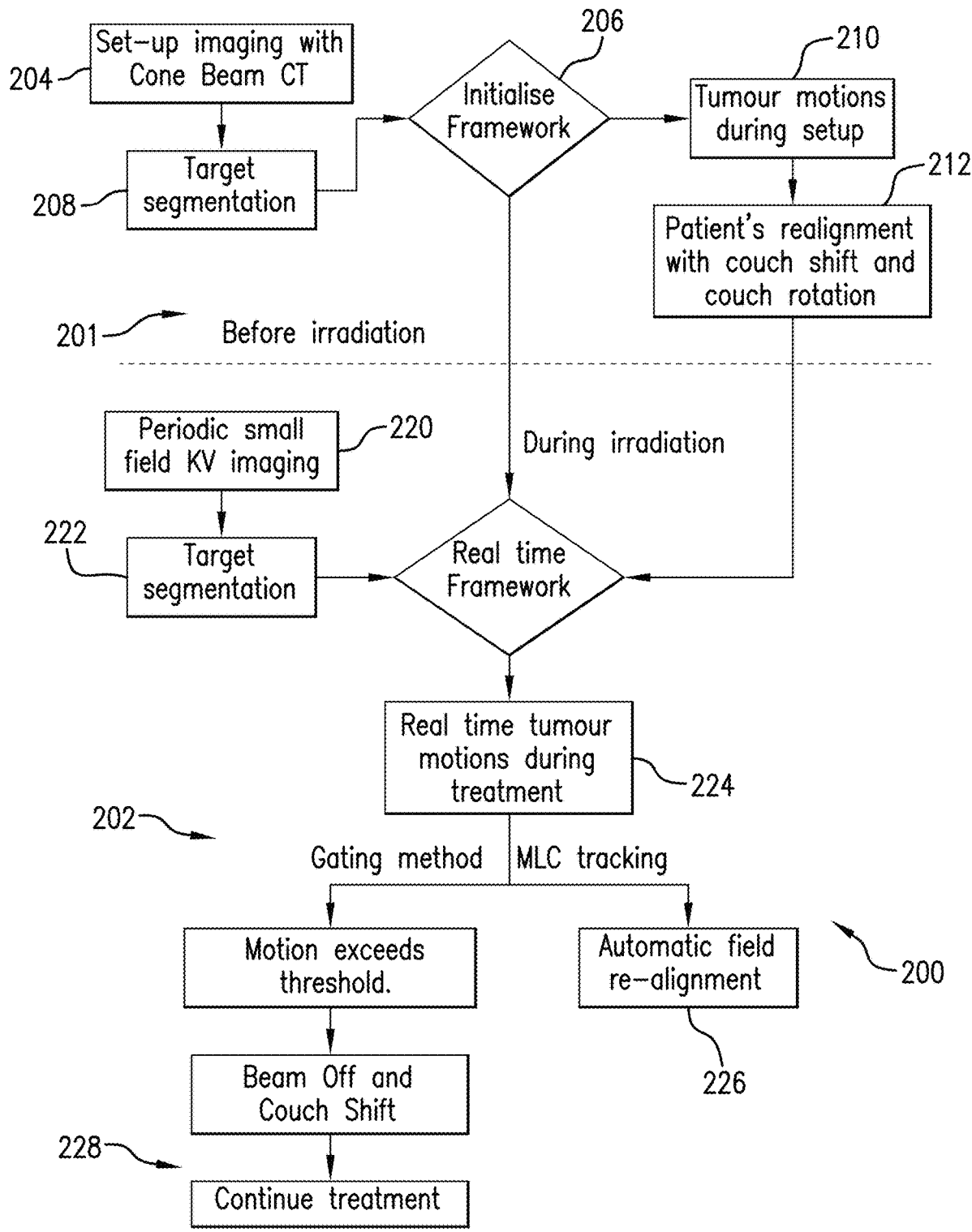
FIG. 2 is a flowchart of a guided radiation therapy process according to an embodiment of the present invention.

FIG. 2 illustrates a method of guided radiation therapy in which the present invention can be practiced. The methods of guided radiation therapy are similar to those followed by Huang et al. 2015 (Huang, C.-Y., Tehrani, J. N Ng, J. A., Booth, J. T. & Keall, P. J. 2015. Six Degrees-of-Freedom Prostate and Lung Tumour Motion Measurements Using Kilovoltage Intrafraction Monitoring. Int J Radiat Oncol Biol Phys, 91, 368-375); and Keall et al. 2016 (Keall, P. J., Ng, J. A., Juneja, P., O'brien, R. T., Huang, C.-Y., Colvill, E., Caillet, V., Simpson, E., Poulsen, P. R., Kneebone, A., Eade, T. & Booth, J. T. 2016. Real-Time 3D Image Guidance Using a Standard LINAC: Measured Motion, Accuracy, and Precision of the First Prospective Clinical Trial of Kilovoltage Intrafraction Monitoring Guided Gating for Prostate Cancer Radiation Therapy. Int J Radiat Oncol Biol Phys, 94, 1015-1021) (the contents of which are each incorporated by reference for all purposes with the exception of the use of the motion tracking method described herein).

The process 200 can be divided into two phases, set up or the learning phase 201 and treatment 202. The learning phase 201 uses an imaging procedure 204, e.g. Cone Beam CT, before treatment to initialise 206 the parameters for a movement tracking framework. As described below, target segmentation 208 is used to identify fiducial markers in the target during initialisation. After initialisation, the method moves to the treatment phase 202. During the treatment phase the treatment beam is activated and the target irradiated, movement tracking system will update the tumour's translational and rotational motion 224 in real-time using the small-field kV images 220. As explained in more detail below, the position of the fiducial markers is identified and this data is used to check and possibly update a position estimation model.

The key component of the marker tracking system is the use of a convolutional neural network (CNN) to detect fiducial markers within kilovoltage (kV) images. The following description outlines the creation of the image datasets used for the CNN training and the network architectures. Two methods of training are described, namely training from scratch and fine-tuning using a pretrained CNN. The workflow for real-time marker tracking using the trained CNN is then described.

Training and Validation Datasets

The training of a CNN requires a large dataset of training images for it to accurately learn the required features. A separate large validation dataset is used after training to assess the accuracy of the CNN on new unseen images. The first pre-processing technique applied to both datasets was the application of a temporal filter to reduce the level of noise (including MV scatter noise). The temporal filter was performed by averaging three consecutive frames.

Each kV image of size 1024×768 pixels is then divided into smaller images of size 32×32 pixels producing 768 training images per kV image. In the case of overlapping markers, each image contained an entire marker and a secondary marker which could be partially or completely within the image. The input size of 32×32 pixels was selected to ensure that the largest type of marker would be fully contained within the smaller images. Then, the smaller images were each normalised to ensure that all images were scaled to the same range, allowing for even feature distributions between all inputs. kV images were normalized using the following equation:

$$\text{normalised image} = \frac{\text{image} - \text{mean(image)}}{\text{std(image)}} \quad (1)$$

For training and validation of arbitrarily shaped marker CNNs, cone beam computed tomography (CBCT) projection images from ten fractions of seven lung cancer patients with implanted coiled markers were used. The CBCT images were normalized using the following equation:

$$I_N = \frac{I - \text{Min}(I)}{\text{Max}(I) - \text{Min}(I)} \quad (2)$$

The two different normalization methods were selected to ensure that the features of the markers would be emphasized for each image modality so as to improve the performance of the CNN Equation 1 subtracts the mean of the pixel values in the original image from each individual pixel. Then each individual pixel is divided by the standard deviation of the pixel values in the original image. After normalisation, each image is rescaled to a 16-bit image. This normalisation process ensures that all images are scaled to the same range, allowing for even feature distributions between all inputs. Finally, these smaller images are labelled as a "marker" or "background" image.

Training and Validation Datasets

I—Cylindrical Shaped Marker Data

Figure 2A:
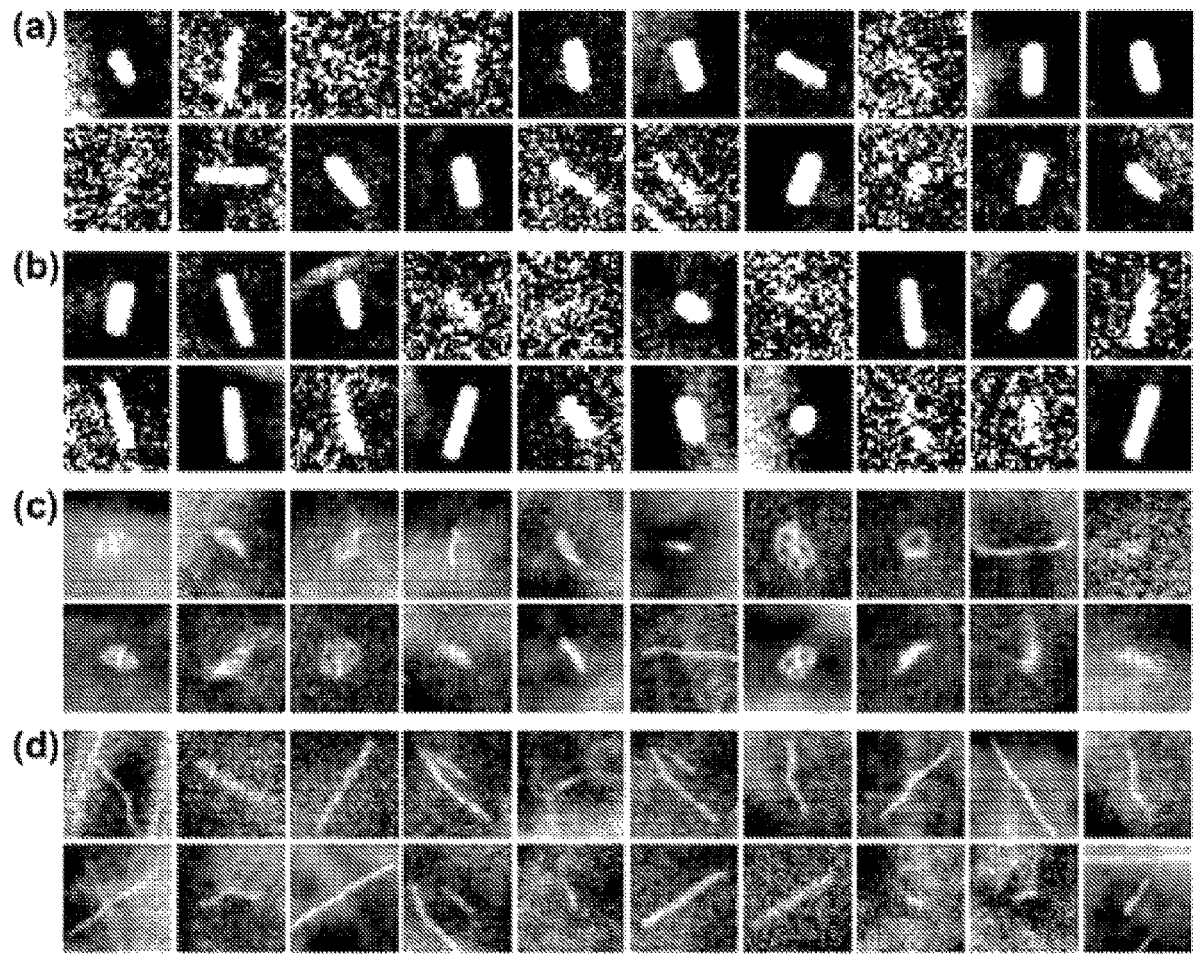
FIG. 2A shows various examples of markers from training and validation datasets.

The cylindrical shaped marker CNNs were trained using intrafraction kV images from a phantom and five fractions from three prostate cancer patients undergoing radiotherapy at the Royal North Shore Hospital, Australia. The patients received either a standard fractionation treatment (80 Gy in 40 fractions) or a boosted high dose treatment (2×25 Gy+23×2 Gy). Each of the patients and the phantom had three implanted cylindrical gold fiducial markers and two patients had overlapping markers. The phantom data had images with varying MV treatment beam levels corresponding to dose rates of 0 monitor units per minute (MU/min), 300 MU/min and 600 MU/min. The lateral width of the phantom, representing pelvic width, was also varied with widths of 35.5 cm, 39.5 cm and 43.5 cm. For both patients and phantom image acquisition, the source to isocenter distance (SID) and source to detector distance (SDD) were set at 100 cm and 180 cm, respectively. The pixel size at the detector was 0.388×0.388 mm$^2$. Thus, the pixel size at isocenter was 0.216×0.216 mm$^2$. Three datasets were generated using the same patient data with additional phantom images of increasing levels of noise. Contrast-to-noise ratios (CNR) were used to quantify the highest level of noise in each dataset. Following pre-processing of the data, each of the three datasets consisted of 30,000 positive and 30,000 negative sub-images. The sub-images were randomly selected out of a larger dataset to balance the training sets. Dataset 1 included images with the lowest levels of noise (CNR=1.6±0.15), dataset 2 included images with moderate levels of noise (CNR=0.33±0.12) and dataset 3 included images with the highest levels of noise (CNR=0.19±0.11) (FIG. 2A (a)).

The CNNs were validated against an unseen dataset of intrafraction fluoroscopic images of prostate cancer patients. The validation dataset includes fluoroscopic intrafraction images from twelve fractions of ten patients with range of pelvic widths from 37 to 40 cm. Six of the patients received the same treatment as the patients used in the training dataset. The four other patients received a high dose treatment (6.25 Gy/fraction) for five fractions. All patients were treated with VMAT on a Varian Trilogy system. Each of the ten patients had three implanted gold fiducial markers and four patients had overlapping markers. In total and following pre-processing, the dataset contained 78,672 positive and 2,207,996 negative sub-images (FIG. 2A (b)).

II—Arbitrarily Shaped Marker Data

CBCT projection images from ten fractions of seven lung cancer patients with one to four implanted Visicoil markers were used for the training and validation of the arbitrarily shaped marker CNNs. For these images, the pixel size at isocenter is 0.259×0.259 mm2 (SDD=150 cm). The training dataset consisted of 100,000 positive and 100,000 negative sub-images derived from six fractions of three patients (FIG. 2A (c)). To create a balanced training dataset, the sub-images were randomly selected out of a larger dataset. The CNNs were validated against 115,288 positive and 1,329,562 negative sub-images from four fractions of the other four unseen patients (FIG. 2A (d)). The training and validation datasets each had eight distinct markers in total.

CNN Architectures

Figure 2B:
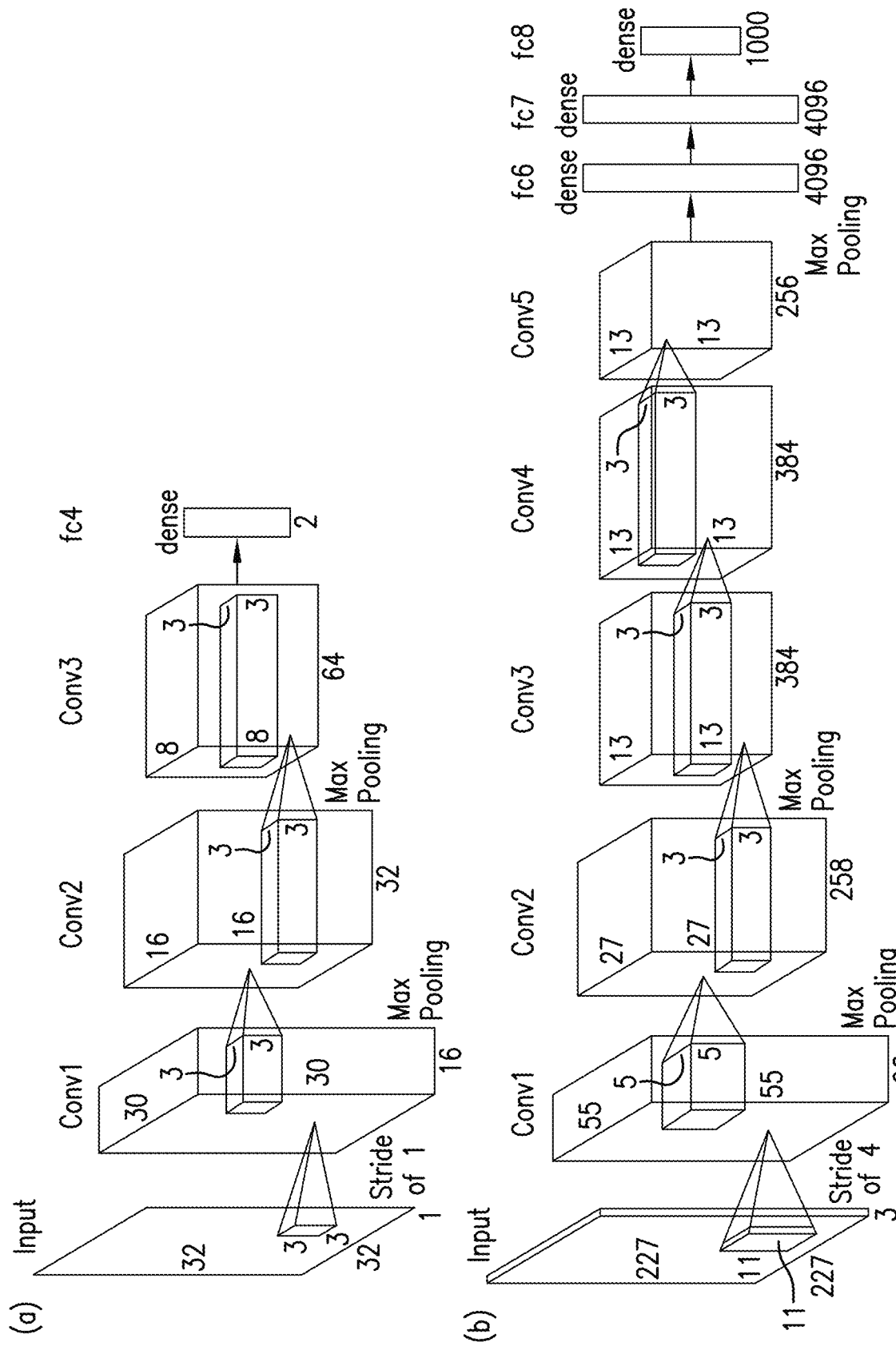
FIG. 2B is a schematic illustration of the CNN architectures that are suitable for practising and/or validating embodiments of the present invention.

The automated tracking according to the invention requires a fast and accurate CNN to detect implanted fiducial markers in real time during radiotherapy. One such architecture that is suitable for practising the present invention is illustrated in FIG. 2B. Various CNN models and training methods were investigated to determine the best performing model in terms of accuracy and speed of marker detection. The CNNs developed are binary classifiers that distinguish between positive images containing a marker and negative-background images. A first CNN model used for full training consists of three convolutional layers, two pooling layers and one fully connected layer (FIG. 2B (a). Three batch normalisation layers and three rectified linear units (ReLU) were used to reduce initialisation sensitivity and accelerate the training of the CNN.

For comparison, transfer learning was performed using 'AlexNet'. AlexNet is a pretrained CNN which has been trained on over a million natural colour images. AlexNet has five convolutional layers with three pooling layers and three fully connected layers (FIG. 2B (b)). Transfer learning involves the transferring of the pre-learnt features to a new application. The last fully connected layer is replaced with a new fully connected layer with two neurons for binary classification. Additional pre-processing of the training and validation datasets was required prior to being used with AlexNet since AlexNet is trained on colour images of size 227×277 pixels. The images in the dataset were thus required to be enlarged from 32×32 pixels to 227×277 pixels and the single grayscale channel was repeated three times to produce a 3-channel RGB image.

The CNNs were trained using the Matlab Neural Network Toolbox™ on a desktop computer with two Intel® Xeon® Gold 6130 processors (2.1 GHz) with 64 GB RAM and a NIVIDIA® Quadro® P6000 Graphics Processing Unit (GPU). A stochastic gradient descent with momentum was used to minimise the error function by updating the weights and biases. A mini-batch sizes of 128 and 256 were used for the stochastic gradient descent algorithm for the training of the cylindrical marker CNNs and arbitrarily shaped marker CNNs respectively. Each network was trained with a constant learning rate of 0.0001 and a momentum of 0.9. The datasets were shuffled before each epoch to ensure that the same data was not discarded every epoch. Early stopping regularization was employed using additional unseen images to avoid overfitting.

The use of the CNN in a radiation therapy system is described by reference to FIG. 3. At step 300, after initiation of the tracking system, the initial position of the markers is defined by the user for the first kV image. The position and number of markers selected is used for the subsequent frames. At step 302, the marker positions are output to image guided radiation therapy system 10 in a suitable format to effect operational control of the system's components (principally the treatment beam and support platform 26). Typically, the data can be formatted in a suitable manner to provide three-dimensional positional information in order to effect motion of radiation therapy system' components along and about three cardinal axes.

Examples of the use of marker positions to effect operational control of the radiation therapy system include:
- estimating motion between the time of capture of individual images so as to perform tracking/targeting at a sub-imaging interval time frame; and
- use in patient set-up;

At step 304, a kV image captured by imaging system 16 during operation of the radiation therapy system 10 is received at the control system 30.

The image is analysed first by generating tracking windows using the previously determined location of the markers. A tracking window is a cropped area which is centred on each individual marker. The tracking window has been found to significantly improve the efficiency of the detection process by reducing the number of regions required to be searched. The size of each tracking window accounts for the movement of the marker in between each frame while not being too large and increasing the number of images which are required to be classified.

Figure 3:
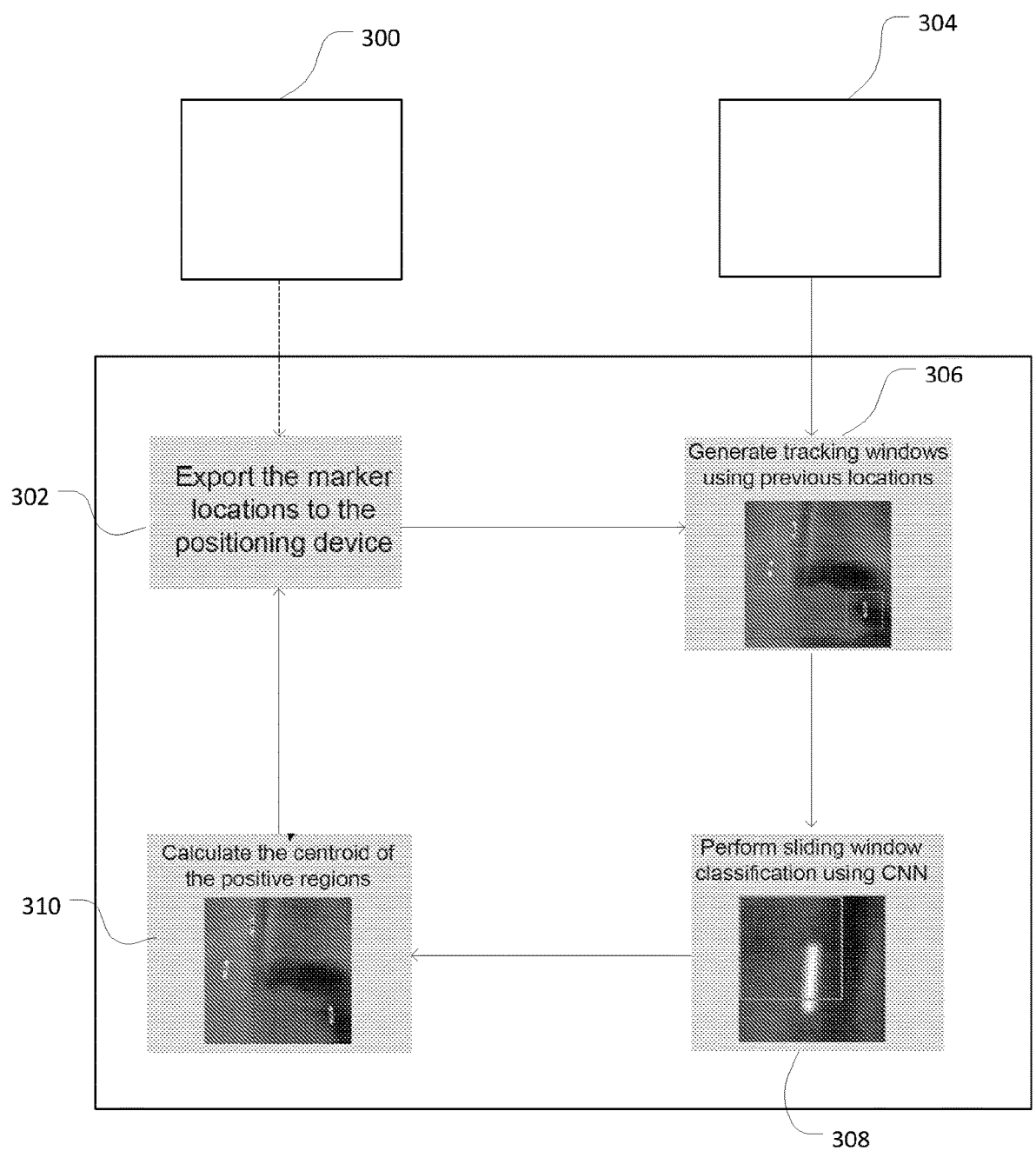
FIG. 3 illustrates an image analysis methodology performed by an embodiment of the present invention.

Each marker has a window of a set size as shown in FIG. 3. The ideal tracking window size for the described embodiment is 46×46 pixels, as it has been found that smaller window sizes reduce the detection accuracy. Conversely, increasing the window size significantly correspondingly decreases the speed of detection, as a larger number of images are required to be classified.

The location of the tracking window is updated every frame by using the marker positions from the previous frame. Currently, the marker detection for each tracking window is performed linearly. However, the speed of detection can by further reduced by processing all of the tracking windows at once in parallel on a CPU.

At step 308, a sliding window-based processing analysis is performed on the portions of the image bounded by each tracking window in order to determine the position of the marker. The sliding window has a size of 32×32 pixels so as to coincide with the input size of the trained CNN. The window begins in the top left corner and moves downwards a pixel at a time. Upon reaching the bottom of the area, the window moves horizontally one pixel and repeats the process. Each time the sliding windows moves, the selected area is cropped and processed in a similar process to training data, in that the image is first normalised using equation 1 or 2 and rescaled to a 16-bit image.

The normalised image is classified as a "marker" or "background" using the trained CNN. If the image is identified to be a "marker", it is classified as positive and if it is identified to be "background", it is classified as negative. The centre location of a positive image is recorded in a logical array to be used later to determine the marker position. This process outlined is repeated until the entire image tracking window has been searched. In the case of overlapping markers, the width of the two tracking windows is reduced as the markers approach to ensure that the approaching markers are not detected in the alternate window. Once the markers begin to separate, the tracking windows separate and gradually increase in width to the original size.

Upon the completion of the sliding window classification (step 310), the position of the marker is determined. This step proceeds by determining the centroid of connected positive regions from the sliding window classification. The calculated centroid is the position of the marker. The x- and y-coordinates of the marker are stored and the method returns to step 302, where the stored coordinates are output to the image guided radiation therapy system 10. The stored coordinates are also utilised in the next iteration of step 306 to generate tracking windows for a newly received image.

Occasionally a marker may not be detected as a result of heavy noise. In this scenario, the position of the marker is set to the previous marker position. If a marker is not detected for a large number of frames, a larger tracking window can be set to increase the search area for the marker.

The trained CNNs were evaluated by classifying all sub-images in the validation datasets as positive (marker) or negative (background). The classifications were compared to the ground truth of the annotated validation datasets. Several analysis methods were employed to determine the performance of the CNNs against unseen validation datasets. The classification performances of the CNNs were evaluated using PRC plots. PRC plots provide a prediction of future performance for classifiers validated on imbalanced datasets. A PRC plot illustrates the relationship between precision (fraction of true positive sub-images among the positive classifications) and recall (also known as sensitivity). The AUC was used to quantify the performance of the CNN where an AUC of 1 indicates perfect classification performance. Furthermore, sensitivity (SN) (fraction of actual positive sub-images that have been correctly classified) and specificity (SP) (fraction of actual negative sub-images that have been correctly classified) of the CNNs were calculated using equations 3 and 4 respectively:

$$SN = TP/TP+FN \quad (3)$$

$$SP = TN/TN+FP \quad (4)$$

where TP is true positives, TN is true negatives, FP is false positives and FN is false negatives.

Furthermore, sensitivity and specificity of the CNNs were calculated. These two analysis methods were used to determine the performance of the CNNs against unseen validation datasets.

In addition, the performance of the cylindrical shaped marker tracking system was evaluated against the ground truth and tracking results for a KIM treatment. The ground truth was constructed using the KIM tracking results and manual segmentation where KIM failed to track markers. The arbitrarily shaped marker tracking system was evaluated against manual segmentation for the ground truth and the segmentation system developed by Poulsen et al (Poulsen P R, Fledelius W, Keall P J, et al. A method for robust segmentation of arbitrarily shaped radiopaque structures in cone-beam CT projections. *Medical Physics.* 2011; 38(4): 2151-2156). The construction of arbitrarily shaped marker template required manual selection of the markers in three to six projections with a large angular separation.

In this regard, the tracking system was tested on one fraction of each patient used in the validation data, with the performance of the cylindrical shaped marker tracking system being evaluated on ten patients against the ground truth. The ground truth was constructed using the KIM tracking results and manual segmentation where the KIM segmentation was inaccurate. The arbitrarily shaped marker tracking system was evaluated on four patients against the ground truth, with the ground truth being constructed using the Poulsen segmentation system and manual segmentation for inaccurate marker positions. This system requires the manual selection of the markers in three to six projections with a large angular separation to construct the arbitrarily shape marker template. The error of tracking system was defined as the CNN detection marker centroid minus the ground truth marker centroid. The errors were calculated in the x- and y-directions and the Euclidian distance. The Euclidian distance is defined as the straight-line distance d between the ground truth and centroid determined by the CNN and is calculated using equation 5:

$$d(c,t) = \sqrt{(t_1-c_1)^2 + (t_2-c_2)^2} \quad (5)$$

where the CNN detection marker centroid location is $c=(c_1, c_2)$ and the true marker centroid location is $t=(t_1, t_2)$.

The overall errors were quantified by the calculation of the mean error and the $1^{st}$ and $99^{th}$ percentiles of the errors. Additionally, the RMSE for each patient was determined using equation 6:

$$RMSE = \sqrt{\frac{\sum_{i=1}^{n}(C_i - T_i)^2}{n}} \quad (6)$$

where C is the CNN detection value, T is the true value and n is the total number of values.

Figure 4A:
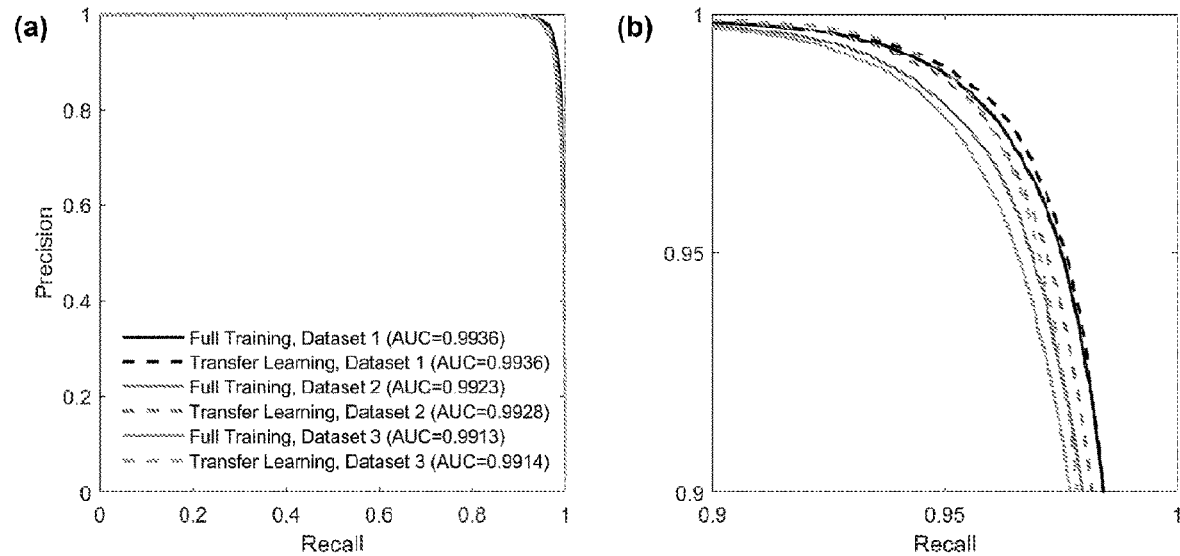
FIG. 4A shows PRC curves on cylindrical shaped marker classification performance for full training and transfer learning approaches. (a) Full PRC curve. (b) Detailed PRC curve.
Figure 4B:
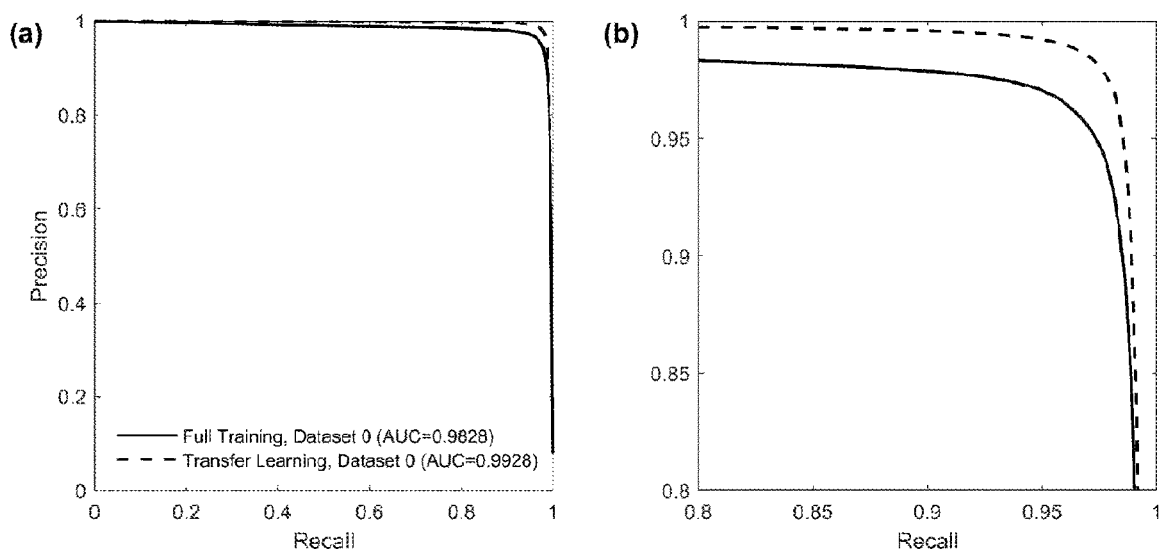
FIG. 4B shows PRC curves on arbitrarily shaped marker classification performance for full training and transfer learning approaches.

The results shown in FIGS. 4A and 4B demonstrate that as the amount of image data used for training increases, the accuracy also increases for both the CNNs trained from scratch and fine-tuned. The trained CNNs had high accuracy with the lowest AUC equal to 0.9994 for the fully trained CNNs and 0.9993 for the transfer learning CNN. High sensitivities and specificities were also achieved for both training methods. The sensitives and specificities ranged from 98.87 to 99.42 and 97.99 to 99.32 respectively. However, no single CNN achieved both the highest sensitivity and specificity. Altering the level of noise in the training data resulted in opposite effects on the sensitivity and specificity. Increasing the level of noise for each fully trained CNN improved the sensitivity and decreased specificity. However, different effects were observed for the transfer learning CNN. Increasing from low (dataset 1) to moderate (dataset 2) improved the sensitivity and decreased specificity. When further increasing to a high level of noise (dataset 3), the trend was the opposite. In terms of AUCs, both training methods achieved comparable results with a difference of 0.0001 between the two training methods on each of the datasets. The AUCs slightly decreased by 0.0002 when training was performed using data with higher MV scatter noise.

FIG. 4A depicts PRC curves on cylindrical shaped marker classification performance for the full training and transfer learning approaches. (a) Full PRC curve. (b) Detailed PRC curve.

The following table summarises classification performance results for the cylindrical shaped marker CNNs for 78,672 positive and 2,207,996 negative samples from twelve fractions of ten patients.

| Training Method | Training Dataset | Sensitivity (%) | Specificity | AUC |
| --- | --- | --- | --- | --- |
| Full training | 1 | 98.87 | 99.32 | 0.9996 |
| Transfer learning | 1 | 99.18 | 98.96 | 0.9995 |
| Full training | 2 | 99.00 | 98.92 | 0.9995 |
| Transfer learning | 2 | 99.42 | 98.13 | 0.9994 |
| Full training | 3 | 99.35 | 97.99 | 0.9995 |
| Transfer learning | 3 | 99.04 | 98.39 | 0.9995 |

The results for the arbitrarily shaped marker CNNs are illustrated in FIG. 4B and the following Table 2. These compare the results of full training and transfer learning for arbitrarily shaped marker CNNs using a large dataset. The transfer learning CNN had the highest AUC of 0.9928 in comparison to 0.9828 for full training. Full training had a higher sensitivity of 98.58% compared to 98.49% for the transfer learning CNN. Transfer learning improved the specificity from 98.97% for full training to 99.56%. Overall, the transfer learning has better performance for arbitrarily shaped markers.

FIG. 4B depicts PRC curves on arbitrarily shaped marker classification performance for full training and transfer learning approaches with FIG. 4B (a) showing the full PRC curve and FIG. 4B(b) showing the detailed PRC curve.

Table 2 summarises classification performance results for the arbitrarily shaped marker CNNs for 115,288 positive and 1,329,562 negative samples from four fractions of four patients.

| Training Method | Sensitivity (%) | Specificity (%) | AUC |
| --- | --- | --- | --- |
| Full training | 98.58 | 98.97 | 0.9828 |
| Transfer learning | 98.49 | 99.56 | 0.9928 |

The speed of classification of the CNNs were evaluated using a laptop system with an Intel® Core™ i7-4720HQ processor (2.60 GHz) with 16 GB RAM and a NIVIDIA GeForce® GTX 970M GPU. The tracking system was implemented with a laptop system to evaluate the performance of the system on the minimum hardware that would be available. The time of classifications included the time for the rasterization and normalization of the images and CNN classification. The compact CNN performed single image classifications faster than AlexNet on a CPU and GPU. For the sliding window classification of one tracking window, AlexNet was over 16 s slower than the compact CNN on a CPU. The difference in the speed of marker segmentation between the two architectures was reduced when classification was performed on a GPU.

Table 3 summarises the Table 3 summarises the mean times for the segmentation of one marker for a 46×46 pixel tracking window size with a step size of 2 pixels. The times are based on classifications using the cylindrical shaped marker CNNs trained on dataset 2.

| CNN Architecture | Segmentation time on CPU (ms) | Segmentation time on GPU (ms) |
| --- | --- | --- |
| Compact | 36 | 9.0 |
| AlexNet | 1400 | 300 |

Figure 4C:
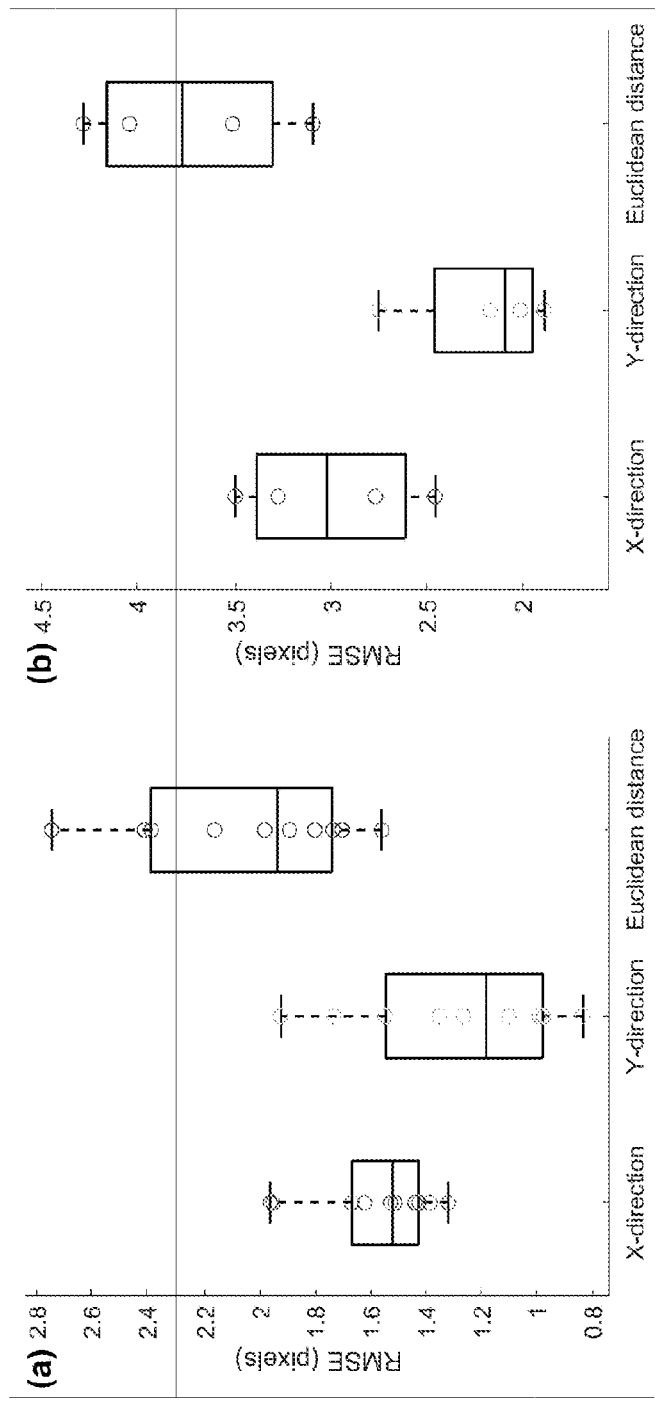
FIG. 4C is a graph of the mean RMSE and the 1st and 99th percentiles of the errors of CNN multiple object tracking.

Following the training of the CNNs, the CNN trained from scratch on dataset 3 was used in the method described by reference to FIG. 3. The errors of the tracking system for cylindrical and arbitrarily shaped markers are presented in Table 4. The arbitrarily shaped marker tracking was observed to be less accurate than the cylindrical marker tracking. The cylindrical shaped marker tracking achieved a lower mean Euclidean distance error of 1.7±1.1 pixels compared to 2.9±2.2 pixels for arbitrarily shaped marker tracking. The RMSE was higher in the x-direction compared to the y-direction for both types of markers (FIG. 4C). The mean error and RMSE is equivalent to sub-millimeter accuracy for both cylindrical and arbitrarily shaped marker tracking.

TABLE 4

Mean error, mean RMSE and the $1^{st}$ and $99^{th}$ percentiles of the errors of CNN multiple object tracking. The errors are calculated in the x- and y-directions and Euclidean distances for cylindrical and arbitrarily shaped markers.

| | Cylindrical Shaped Marker | | | Arbitrarily Shaped Markers | | |
| --- | --- | --- | --- | --- | --- | --- |
| | X-direction | Y-direction | Euclidean Distance | X-direction | Y-direction | Euclidean Distance |
| Mean Error (pixels) | −0.8 ± 1.3 | 0.3 ± 1.2 | 1.7 ± 1.1 | −0.9 ± 2.8 | 0.2 ± 2.2 | 2.9 ± 2.2 |
| Mean RMSE (pixels) | 1.6 ± 0.2 | 1.3 ± 0.4 | 2.0 ± 0.4 | 3.0 ± 0.5 | 2.2 ± 0.4 | 3.7 ± 0.5 |
| $1^{st}$ Percentile (pixels) | −4.0 | −3.0 | 0.0 | −8.0 | −5.0 | 0.0 |
| $99^{th}$ Percentile (pixels) | 3.0 | 4.0 | 5.4 | 5.0 | 6.0 | 10.0 |

Figure 5:
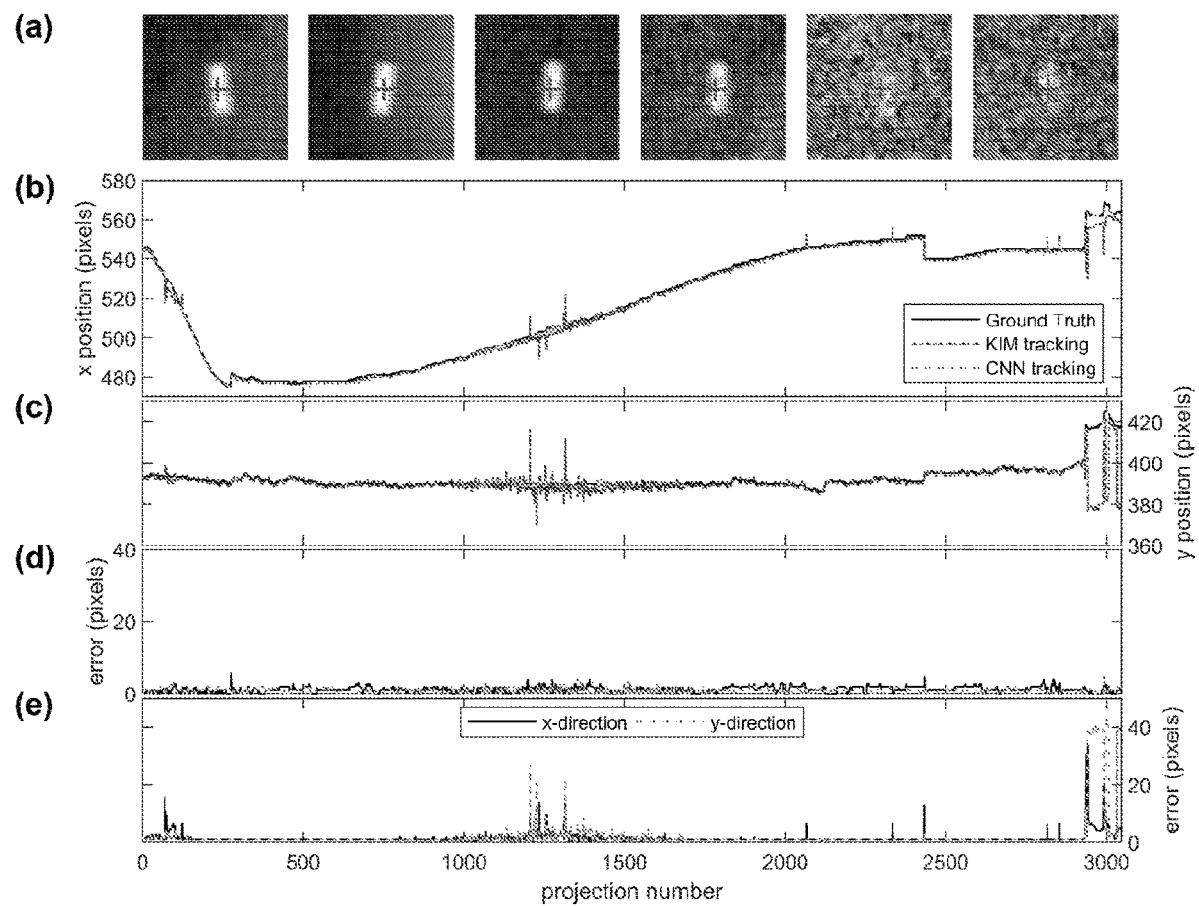
FIG. 5 is an illustrative example of the present invention when used to track cylindrical shaped fiducial markers throughout a radio therapy treatment fraction.
Figure 6:
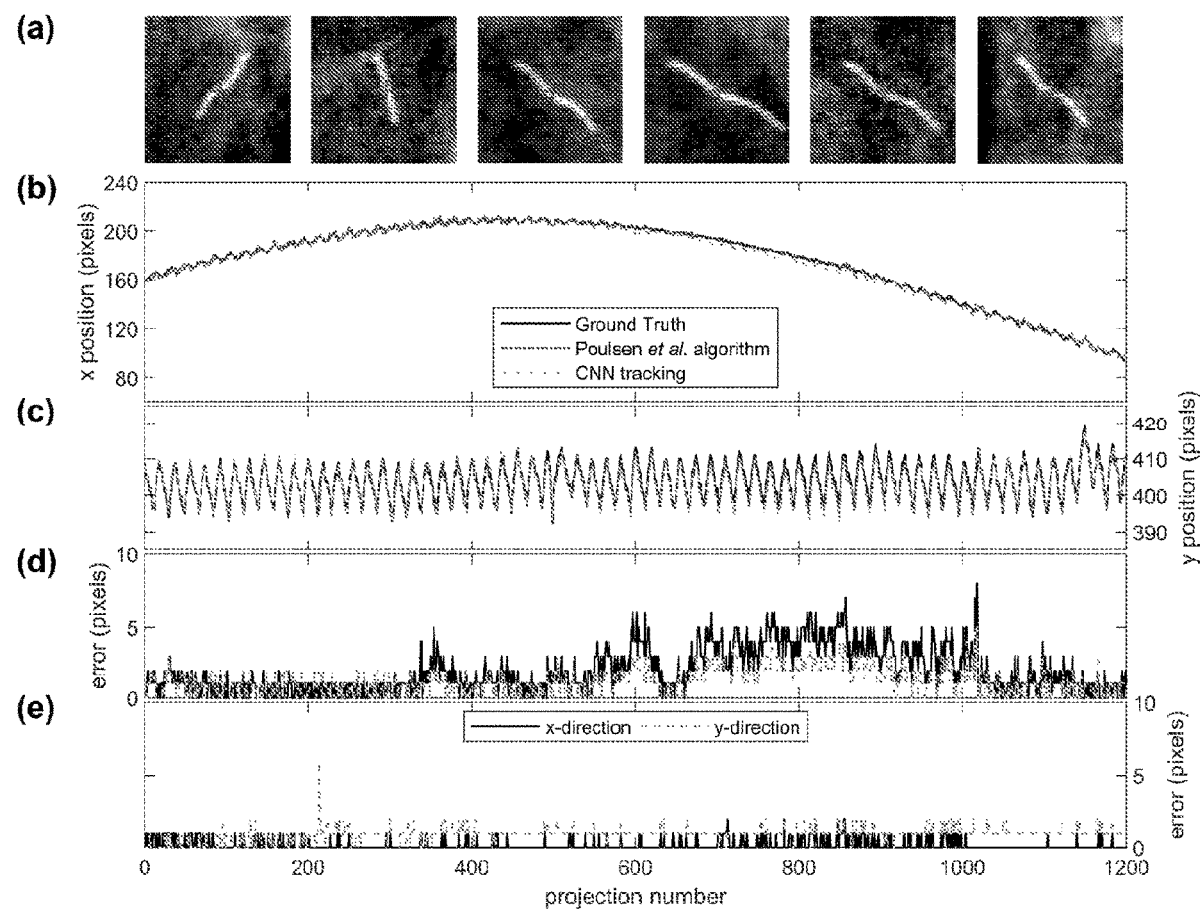
FIG. 6 is an illustrative example of the present invention when used to track arbitrarily shaped fiducial markers throughout a radio therapy treatment fraction.

The results presented in FIGS. 5 and 6 show the example tracking results for one cylindrical and one arbitrarily shaped marker respectively. The KIM system did not accurately track the cylindrical shaped marker during one treatment session of one patient (FIG. 5). For this fraction, our tracking system was able to maintain tracking throughout the fraction. FIG. 5(a) shows sample kV images of the detection of a cylindrical shaped marker using the CNN tracking algorithm. FIGS. 5(b) and 5(c) show 2D trajectory in the x- and y-direction of the marker using the CNN tracking in comparison to the ground truth and KIM treatment tracking, respectively. FIG. 5(d) shows the error between the CNN tracking and the ground truth. (e) Error between KIM treatment tracking and the ground truth.

FIG. 6. (a) shows sample CBCT projections of the detection of an arbitrarily shaped Visicoil marker using the CNN tracking algorithm. The 2D trajectory (x direction) is shown in FIG. 5 (b), with the y-direction of the marker using the CNN tracking in comparison to the ground truth and Poulsen algorithm, being shown in FIG. 6 (c). The error between the CNN tracking and the ground truth is shown in FIG. 6(d) and the error between Poulsen et al. algorithm and ground truth shown in FIG. 6(e).

It will be realized that the fully trained CNN was successfully used in a real-time multiple object tracking system that can be applied to intrafraction monitoring applications. FIGS. 5 and 6, and Table 4 demonstrate initial tests of the CNNs in a simple tracking system to track markers with gantry rotation. The cylindrical and arbitrarily shaped markers were successfully tracked throughout the treatment fractions. Sub-millimeter accuracy was achieved for all three cylindrical and two arbitrarily shaped marker CNNs.

The high accuracy for the detection and tracking of arbitrarily shaped markers shows the potential to track other types of markers such as liquid markers. Furthermore, the present invention can be applied to track the tumor itself, removing the need for implanted markers. This would eliminate the cost and discomfort of the marker implantation and would allow radiotherapy to commence without the delay of the marker implantation procedure. The deep-learning framework according to the invention could also be expanded to tracking abdominal markers in the liver, pancreas and kidneys since the motion within the training set does not affect the performance. This approach could also be used in a hybrid system where the CNN is used to augment template-based segmentation by optimizing the position and size of the search area.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method for guiding a radiation therapy system, comprising:
  capturing an image of a target area to which radiation is to be delivered and of one or more objects of interest within or about the target area, the capturing configured to include a respective object of interest image for each of the one or more objects of interest;
  analyzing the image with a trained convolutional neural network (CNN) having a CNN input window size, the analyzing comprising
    accessing in a data storage one or more stored positions, each stored position of the one or more stored positions being for a respective object of interest of the one or more objects of interest, and having been previously determined from a previously captured image of the target area and the one or more objects of interest within or about the target area,
    generating, for each object of interest of the one or more objects of interest, a respective tracking window positioned on the image according to the stored position of the object of interest, bounding a respective interior having a size that is larger than the CNN input window size, larger than a size of the object of interest image, and traversable in two dimensions by the trained CNN, and
    traversing, for each object of interest of the one or more objects of interest, the respective interior of the respective tracking window with the trained CNN, in the two dimensions, based at least in part on a result of the traversing the respective interior, generating an updated position data for the object of interest; and
  outputting to the radiation therapy system the updated position data for each object of interest of the one or more of the objects of interest, or providing to the radiation therapy system one or more adjusted radiation therapy system operating parameters based at least in part on the updated position for the one or more objects of interest, or both.

2. A method according to claim 1, wherein at least one stored position of the one or more stored positions was previously determined from an earlier application of the CNN to the previously captured image.

3. A method according to claim 1, wherein the generating the respective tracking window for each object of interest of the one or more objects of interest one or more tracking windows is configured such that, for each of the tracking windows, the stored position of the respective object of interest is substantially centered in the tracking window.

4. A method according to claim 1, wherein the traversing the respective interior of the respective tracking window comprises:
  a) positioning the CNN on a present region among a plurality of regions within the respective interior of the tracking window, each of the regions of the plurality of regions partially overlapping at least one other of the regions and having a size corresponding to the input window size of the trained CNN;
  b) based on applying the CNN to the present region, classifying the present region between being a positive region presently including the tracking window's respective object of interest and a negative region not presently including the tracking window's respective object of interest;
  c) sliding the trained CNN an incremental distance to a next region among the plurality of regions;
  d) setting the next region as the present region;
  e) responsive to the present region being an ending region within the respective interior, proceeding to (f), else repeating steps (b) through (e);
  f) determining adjacent ones of the regions classified as positive regions as being connected regions; and
  g) determining a centroid of the connected regions,
  wherein generating the updated position data for the object of interest is further based, at least in part, on a result of the determining the centroid.

5. A method according to claim 4, further comprising normalizing and rescaling the present regions prior to the classifying.

6. A method according to claim 1, wherein, for at one object of interest of the one or more objects of interest, the CNN traversing the respective interior of the respective tracking window further includes the step of reducing a dimension of the tracking window in accordance with the CNN input window size.

7. A method according to claim 1, wherein the trained CNN is trained for objects of interest that include a fiducial marker, or a tumor, or one or more intrinsic anatomical features, or any combination or sub-combination thereof.

8. A method according to claim 1, wherein the image is an x-ray image.

9. A method according to claim 1, wherein the radiation therapy system is a real-time image-guided radiation therapy system.

10. A method according to claim 1, wherein the trained CNN includes three convolutional layers, two pooling layers, and one fully connected layer.

11. A method according to claim 10, wherein the CNN further includes a plurality of batch normalization layers and rectified linear units.

12. A method according to claim 1, further comprising:
  estimating or updating an estimate of a position of the target area to which radiation is to be delivered based at least in part on the updated position data for the one or more of the objects of interest.

13. A method according to claim 12, further comprising the steps of:
  directing at least one treatment beam from the radiation therapy system based at least in part on the estimated or the updated estimate of the position of the target area.

14. The method of claim 13, further including the steps of:
  a) redefining the previously determined image to be said image and updating the stored one or more stored positions, in the data storage, in accordance with the updated position data for each object of interest of the one or more objects of interest;
  b) capturing a next image of the target area and of the one or more objects of interest within or about the target area, the capturing the next image configured to include a respective object of interest next image for each of the one or more objects of interest;
  c) performing a tracking analysis of the next image with the trained CNN, comprising steps of accessing in the data storage the one or more stored positions, each for a respective object of interest of the one or more objects of interest, generating, for each of the one or more objects of interest, a respective next image tracking window positioned on the next image according to the stored position of the object of interest, bounding a respective next interior having a size that is larger than the CNN input window size, larger than a size of the respective object of interest next image, and traversable in the two dimensions by the trained CNN, and traversing, for each object of interest of the one or more objects of interest, the respective next interior of the respective next image tracking window with the trained CNN, in the two dimensions and generating, based at least in part on a result of the traversing the respective next interior, a next updated position data for the object of interest;

d) outputting a next a next tracking frame, comprising the updated position data for each object of interest of the one or more objects of interest;

e) successively repeating the sequence of steps (a) through (d) to output a succession of next tracking frames and correspondingly tracking the target area by reference to the output succession of next tracking frames over time and directing the at least one treatment beam at the target area based on said tracking.

15. The method of claim 13 wherein directing the at least one treatment beam based at least in part on the estimated or the updated estimate of the position of the target area includes adjusting or setting one or more of the following parameters of the radiation therapy system:

at least one geometrical property of said at least one treatment beam;

a position of the target area relative to the at least one treatment beam;

a time of emission of the at least one treatment beam; and an angle of emission of the at least one treatment beam relative to the target area about a system rotational angle.

16. A method according to claim 1, further comprising:

detecting, based at least in part on the result of the traversing the respective interior of the tracking window, a non-detection of the object of interest; and based at least in part on the detecting the non-detection, to increase the size of the respective interior.

17. A system for guided radiation therapy, comprising:

a radiation source for emitting at least one treatment beam of radiation;

an imaging system arranged to generate an initial image followed by generating a succession of images of a target area to which the treatment beam is to be directed and of one or more objects of interest within or about the target area; and a control system configured to:

receive and store, in a data storage, position for each of the one or more objects of interest, as a stored position;

receive the succession of images from the imaging system and, for each image in the succession, perform an analyzing of the image with a trained convolutional neural network (CNN) having a CNN input window size to successively determine an updated position data for each of the one or more objects of interest; and adjust the guided radiation therapy system using the successively determined updated position data to direct the treatment beam at the target area, wherein the analyzing of each image is as a next image, and comprises steps of:

a) accessing in the data storage the one or more stored positions, each for a respective object of interest of the one or more objects of interest, b) generating, for each of the one or more objects of interest, a respective next image tracking window positioned on the next image according to the stored position of the object of interest, bounding a respective next interior having a size that is larger than the CNN input window size, larger than a size of an image of the object of interest in the next image, and traversable in the two dimensions by the trained CNN, and c) traversing, for each object of interest of the one or more objects of interest, the respective next interior of the respective next image tracking window with the trained CNN, in the two dimensions and, based at least in part on a result of the traversing, generating a next updated position data for the object of interest; and output the updated position data for each object of interest of the one or more objects of interest.

18. A computer software product comprising one or more computer-readable non-transitory storage media storing a sequence of processor-executable instructions that when executed by one or more processors, cause the one or more processors to:

receive an image from a radiation therapy system of a target area to which radiation is to be delivered and of one or more objects of interest within or about the target area;

analyze the image with a trained convolutional neural network (CNN) having a CNN input window size, including to:

access in a data storage a respective stored position for each object of interest of the one or more objects of interest, the respective stored position having been previously determined from a previously captured image of the target area and the one or more objects of interest within or about the target area, generate one or more tracking windows, wherein each tracking window of the one or more tracking windows corresponds to a particular object of interest of the one or more objects of interest and is positioned on the image according to the respective stored position of the particular object of interest of the one or more objects of interest, bounds a respective interior having a size larger than the CNN input window size, larger than a size of the respective object of interest image, and which is traversable in two dimensions by the trained CNN, and for each tracking window of the one or more tracking windows, to:

traverse the respective interior with the trained CNN, in the two dimensions, and generate an updated position data of the respective object of interest, based at least in part on a result of the traverse of the respective interior with the trained CNN; and output to the radiation therapy system the updated position data for each object of interest of the one or more objects of interest, or provide to the radiation therapy system one or more adjusted radiation therapy system operating parameters based at least in part on the updated position data for the one or more objects of interest.

19. A method for guiding a radiation therapy system, comprising:
- capturing an image of a target area and within or about the target area a fiducial marker, the capturing configured such that the image contains a fiducial marker image having a fiducial marker image size;
- analyzing the image with a trained convolutional neural network (CNN) having a CNN input window size, the analyzing comprising
  - accessing in a data storage a stored position for the fiducial marker, a stored position that had been previously determined from a previously captured image of the target area and the fiducial marker within or about the target area,
  - generating a tracking window, positioned on the image according to the stored position for the fiducial marker, the tracking window bounding an interior having a size larger than the CNN input window size, larger than the fiducial marker image size, and which is traversable in two dimensions with the trained CNN,
  - traversing the interior with the CNN, in the two dimensions, and
  - generating an updated position data for the fiducial marker based at least in part on a result of the traversing the interior with the trained CNN; and
- outputting to the radiation therapy system the updated fiducial marker position data or providing to the radiation therapy system one or more adjusted radiation therapy system operating parameters that are based at least in part on the updated fiducial marker position data, or both.

* * * * *